United States Patent
Boussiotis et al.

(10) Patent No.: US 6,576,236 B1
(45) Date of Patent: Jun. 10, 2003

(54) METHODS FOR STIMULATING T CELL RESPONSES BY MANIPULATING A COMMON CYTOKINE RECEPTOR γ CHAIN

(75) Inventors: Vassiliki A. Boussiotis, Brookline, MA (US); Lee M. Nadler, Newton, MA (US)

(73) Assignee: Dana Farber Cancer Institute, Boston, MA (US)

( * ) Notice: Subject to any disclaimer, the term of this patent is extended or adjusted under 35 U.S.C. 154(b) by 0 days.

(21) Appl. No.: 08/270,152

(22) Filed: Jul. 1, 1994

(51) Int. Cl.$^7$ .................... A61K 39/395; C07K 16/28

(52) U.S. Cl. .................... 424/154.1; 424/130.1; 424/141.1; 424/143.1; 424/144.1; 424/153.1; 424/154.1; 424/173.1; 530/387.1; 530/388.1; 530/388.2; 530/388.22; 530/388.7; 530/388.73; 530/388.75; 530/389.1; 530/389.6

(58) Field of Search .................... 424/130.1, 141.1, 424/143.1, 154.1, 173.1, 153.1; 514/2, 8; 530/351, 388.22, 388.75, 387.1

(56) References Cited

U.S. PATENT DOCUMENTS 5,017,691 A * 5/1991 Lee et al.
5,229,115 A * 7/1993 Lynch
5,382,427 A * 1/1995 Plunkett et al.
5,474,769 A * 12/1995 Grabstein et al.

FOREIGN PATENT DOCUMENTS

WO    WO 90/05541    5/1990

OTHER PUBLICATIONS

Goroff et al. J. Immunol. 146: 18–25, (1991).*
Yashwant et al. Immunol Today 18: 127–135, (1997).*
Kirken, R., et al., "Characterization of an Interleukin–2 (IL–2)–induced Tyrosine Phosphorylated 116–kDa Protein Associated with the IL–2 Receptor β–Subunit," *The Journal of Biological Chemistry*, vol. 268, No. 30, 22765–22770 (1993).
Kondo, M., et al., "Sharing of the Interleukin–2 (IL–2) Receptor γ Chain Between Receptors for IL–2 and IL–4," *Science*, vol. 262, 1874–1877 (1993).
Takeshita, T, et al., "Cloning of the γ Chain of the Human IL–2 Receptor," *Science*, vol. 257, 379–382 (1992).
Basker, S. et al. PNAS 90: 5687–5690 (1993).
Boussiotis et al. Research in Immunology 146: 140–149 (1995).*
Bluestone Immunity 2: 555–559 (1995).*
Russell et al. Science 262: 1880–1883 (1993).*
Boussiotis et al. Science 266: 1039–1042 (1994).*
Nakarai, T., et al., (1994) "Interleukin 2 Receptor γ Chain Expression on Resting and Activated Lymphoid Cells", *J. Exp. Med.*, vol. 180, pp. 241–251.

Ihle, J.N., et al., (1994) "Signaling by the cytokine receptor superfamily: JAK's and STAT's", *TIBS*, vol. 19, pp. 222–227.
DiSanto, J.P., et al., (1994) "Interleukin–2 (IL–2) receptor γ chain mutations in X–linked severe combined immunodeficiency disease result in the loss of high–affinity IL–2 receptor binding", *Eur. J. Immunol.*, vol. 24, pp. 475–479.
Voss, S.D., et al., (1994) "Severe Combined Immunodeficiency, Interleukin–2 (IL–2), and the IL–2 Receptor: Experiments of Nature Continue to Point the Way", *Blood*, vol. 83, No. 3, pp. 626–635.
Nelson, B.H., et al., (1994) "Cytoplasmic domains of the Interleukin–2 receptor β and γ chains mediate the signal for T–cell proliferation", *Nature*, vol. 369, pp. 333–336.
Nakamura, Y., et al., (1994) "Heterodimerization of the IL–2 receptor β– and γ–chain cytoplasmic domains is required for signaling", *Nature*, vol. 369, pp. 330–333.
Cao, X., et al., (1993) "Characterization of cDNAs encoding the murine interleukin 2 receptor (IL–2R) γ chain: Chromosomal mapping and tissue specificity of IL–2R γ chain expression", *Proceedings of the National Academy of Sciences*, vol. 90, pp. 8464–8468.
Shahinian, A., et al., (1993) "Differential T Cell Costimulatory Requirements in DC28–Deficient Mice", *Science*, vol. 261, pp. 609–612.
Puck, J.M., et al., (1993) "The interleukin–2 receptor γ chain maps to Xq13.1 and is mutated in X–lined severe combined immunodeficiency, SCIDX1", *Human Molecular Genetics*, vol. 2, No. 8, pp. 1099–1104.
Noguchi, M., et al., (1993) "Interleukin–2 Receptor γ Chain Mutation Results in X–Linked Severe Combined Immunodeficiency in Humans", *Cell*, vol. 73, pp. 147–157.
Boussiotis, V.A., et al., (1993) "B7 But Not Intercellular Adhesion Molecule–1 Costimulation Prevents the Induction of Human Alloantigen–specific Tolerance", *J. Exp. Med.*, vol. 178, pp. 1753–1763.

(List continued on next page.)

Primary Examiner—Phillip Gambel
(74) Attorney, Agent, or Firm—Lahive & Cockfield, LLP; Giulio A. DeConti, Jr., Es; DeAnn F. Smith, Esq.

(57) ABSTRACT

When stimulated through the T cell receptor(TCR)/CD3 complex without requisite costimulation through the CD28/B7 interaction, T cells enter a state of antigen specific unresponsiveness or anergy. This invention is based, at least in part, on the discovery that signaling though a common cytokine receptor γ chain (e.g., interleukin-2 receptor, interleukin-4 receptor, interleukin-7 receptor) prevents the induction of T cell anergy. This γ chain has been found to be associated with a JAK kinase having a molecular weight of about 116 kD (as determined by sodium dodecyl sulfate polyacrylamide gel electrophoresis) and signaling through the γ chain induces phosphorylation of the JAK kinase. Accordingly, methods for stimulating or inhibiting proliferation by a T cell which expresses a cytokine receptor γ chain are disclosed.

11 Claims, 4 Drawing Sheets

OTHER PUBLICATIONS

Tan, P., et al., (1993) "Induction of Alloantigen–specific Hyporesponsiveness in Human T Lymphocytes by Blocking Interaction of CD28 with Its Natural Ligand B7/BB1", *J. Exp. Med.,* vol. 177, pp. 165–173.

Gimmi, C.D., et al., (1993) "Human T–cell clonal anergy is induced by antigen presentation in the absence of B7 costimulation", *Proceedings of the National Academy of Sciences,* vol. 90, pp. 6586–6590.

Harpur, A.G., et al., (1992) "JAK2, a third member of the JAK family of protein tyrosine kinases", *Oncogene,* vol. 7, pp. 1347–1353.

Harding, F.A., et al., (1992) "CD28–mediated signaling co–stimulates murine T cells and prevents induction of anergy in T–cell clones", *Nature,* vol. 356, pp. 607–609.

Beverly, B., et al., (1992) "Reversal of in vitro T cell clonal anergy by IL–2 stimulation", *International Immunology,* vol. 4, No. 6, pp. 661–671.

Schorle, H., et al., (1991) "Development and function of T cells in mice rendered interleukin–2 deficient by gene targeting", *Nature,* vol. 352, pp. 621–624.

Kühn, R., et al., (1991) "Generation and Analysis of Interleukin–4 Deficient Mice", *Science,* vol. 254, pp. 707–710.

Wilks, A.F., et al., (1991) "Two Novel Protein–Tyrosine Kinases, Each with a Second Phosphotransferase–Related Catalytic Domain, Define a New Class of Protein Kinase", *Molecular and Cellular Biology,* vol. 11, No. 4, pp. 2057–2065.

June, C.H., (1991) "Signal transduction in T cells", *Current opinion in Immunology,* vol. 3, pp. 287–293.

Firmbach–Kraft, I., et al., (1990) "*tyk2,* prototype of a novel class of non–receptor tyrosine kinase genes", *Oncogene,* vol. 5, pp. 1329–1336.

Ledbetter, J.A., et al., (1990) "CD28 Ligation in T–Cell Activation: Evidence for Two Signal Transduction Pathways", *Blood,* vol. 75, No. 7, pp. 1531–1539.

Schwartz, R.H., et al., (1990) "A Cell Culture Model for T Lymphocyte Clonal Anergy", *Science,* vol. 248, pp. 1349–1356.

June, C.H., et al., (1990) "Role of the CD28 receptor in T–cell activation", *Immunology Today,* vol. 11, No. 6, pp. 211–216.

June, C.H., et al., (1989) "Evidence for the involvement of three distinct signals in the induction of IL–2 gene expression in human T lymphocytes", *The Journal of Immunology,* vol. 143, No. 1, pp. 153–161.

Essery, G., et al., (1988) "Interleukin–2 can prevent and reverse antigen–induced unresponsiveness in cloned human T lymphocytes", *Immunology,* vol. 64, pp. 413–417.

* cited by examiner

*IP Ab:* αIL-2Rγ

IL-2  IL-4  IL-7

— 116

— 66

*Blot Ab:* 4G10

— 116

*Blot Ab:* R80

— 116

*Blot Ab:* JAK1

— 116

*Blot Ab:* JAK2

— 116

*Blot Ab:* TyK2

METHODS FOR STIMULATING T CELL RESPONSES BY MANIPULATING A COMMON CYTOKINE RECEPTOR γ CHAIN

GOVERNMENT FUNDING

Work described herein was supported under National Institute of Health R01 40416 and CA 34183 awarded by the National Institutes of Health. The U.S. government therefore may have certain rights in this invention.

BACKGROUND OF THE INVENTION

The induction of antigen-specific T cell responses involves multiple interactions between cell surface receptors on T cells and ligands on antigen presenting cells (APCs). The primary interaction is between the T cell receptor (TCR)/CD3 complex on a T cell and a major histocompatibility complex (MHC) molecule/antigenic peptide complex on an antigen presenting cell. This interaction triggers a primary, antigen-specific, activation signal in the T cell. In addition to the primary activation signal, induction of T cell responses requires a second, costimulatory signal. In the absence of proper costimulation, TCR signalling can induce a state of anergy in the T cell. Subsequent appropriate presentation of antigen to an anergic T cell fails to elicit a proper response (see Schwartz, R. H. (1990) *Science* 248:1349).

A costimulatory signal can be triggered in a T cell through a T cell surface receptor, such as CD28. For example, it has been demonstrated that suboptimal polyclonal stimulation of T cells (e.g. by anti-CD3 antibodies or phorbol ester, either of which can provide a primary activation signal) can be potentiated by crosslinking of CD28 with anti-CD28 antibodies (Linsley, P. S. et al. (1991) *J. Exp. Med.* 173:721; Gimmi, C. D. et al. (1991) *Proc. Natl. Acad. Sci. USA* 88:6575). Moreover, stimulation of CD28 can prevent the induction of anergy in T cell clones (Harding, F. A. (1992) *Nature* 356:607–609). Natural ligands for CD28 have been identified on APCs. CD28 ligands include members of the B7 family of proteins, such as B7-1(CD80) and B7-2 (B70) (Freedman, A. S. et al. (1987) *J. Immunol.* 137:3260–3267; Freeman, G. J. et al. (1989) *J. Immunol.* 143:2714–2722; Freeman, G. J. et al. (1991) *J. Exp. Med.* 174:625–631; Freeman, G. J. et al. (1993) *Science* 262:909–911; Azuma, M. et al. (1993) *Nature* 366:76–79; Freeman, G. J. et al. (1993) *J. Exp. Med.* 178:2185–2192). In addition to CD28, proteins of the B7 family have been shown to bind another surface receptor on T cells related to CD28, termed CTLA4, which may also play a role in T cell costimulation (Linsley, P. S. (1991) *J. Exp. Med.* 174:561–569; Freeman, G. J. et al. (1993) *Science* 262:909–911).

The elucidation of the receptor:ligand relationship of CD28/CTLA4 and the B7 family of proteins, and the role of this interaction in costimulation, has led to therapeutic approaches involving manipulation of the extracellular interactions of surface receptors on T cells which bind costimulatory molecules. For example, a CTLA4Ig fusion protein, which binds to both B7-1 and B7-2 and blocks their interaction with CD28/CTLA4, has been used to inhibit ejection of allogeneic and xenogeneic grafts (see e.g., Turka, L. A. et al. (1992) *Proc. Natl. cad. Sci. USA* 89:11102–11105; Lenschow, D. J. et al. (1992) *Science* 257:789–792). Similarly, antibodies reactive with B7-1 and/or B7-2 have been used to inhibit T cell proliferation and IL-2 production in vitro and inhibit primary immune responses to antigen in vivo (Hathcock K. S. et al. (1993) *Science* 262:905–907; Azuma, M. et al. (1993) *Nature* 366:76–79; Powers, G. D. et al. (1994) *Cell. Immunol.* 153:298–311; Chen C. et al. (1994) *J. Immunol.* 152:2105–2114). Together, these studies indicate the costimulatory pathway mediated by T cell surface receptors which bind costimulatory molecules such as B7-1 and B7-2 are desirable targets for manipulating immune responses. Delivery of an antigen specific signal to a T cell in the absence of a costimulatory signal does not induce a T cell response, but rather has been found to induce a state of T cell unresponsiveness or anergy (see Schwartz, R. H. (1990) *Science* 248:1349; Jenkins, M. K. et al. (1988) *J. Immunol.* 140:3324). In a number of clinical situations it is desirable to inhibit T cell responses (e.g., in transplantation or autoimmune disorders). Thus, therapeutic approaches have been proposed to induce antigen specific T cell unresponsiveness by blocking of a costimulatory signal in T cells. For example, a CTLA4Ig fusion protein, which binds both B7-1 and B7-2, has been used to inhibit rejection of allogeneic and xenogeneic grafts (see e.g., Turka, L. A. et al. (1992) *Proc. Natl. Acad. Sci. USA* 89, 11102–11105; Lenschow, D. J. et al. (1992) *Science* 257, 789–792). Similarly, antibodies reactive with B7-1 and/or B7-2 have been used to inhibit T cell proliferation and IL-2 production in vitro and inhibit primary immune responses to antigen in vivo (Hathcock K. S. et al. (1993) *Science* 262, 905–907; Azuma, M. et al. (1993) *Nature* 36:76–79; Powers, G. D. et al. (1994) *Cell. Immunol.* 153, 298–311; Chen C. et al. (1994) *J. Immunol.* 152, 2105–2114).

SUMMARY OF THE INVENTION

When stimulated through the T cell receptor(TCR)/CD3 complex without requisite costimulation through the CD28/B7 interaction, T cells enter a state of antigen specific unresponsiveness or anergy. This invention is based, at least in part, on the discovery that signaling though a common cytokine receptor γ chain (e.g., interleukin-2 receptor, interleukin-4 receptor, interleukin-7 receptor) prevents the induction of T cell anergy. This γ chain has been found to be associated with a JAK kinase having a molecular weight of about 116 kD (as determined by sodium dodecyl sulfate polyacrylamide gel electrophoresis) and signaling through the γ chain induces phosphorylation of the JAK kinase.

Accordingly, one embodiment of this invention pertains to methods for stimulating proliferation by a T cell which expresses a cytokine receptor γ chain and which has received a primary activation signal under conditions which normally result in unresponsiveness in the T cell (i.e., lack of costimulation). T cell unresponsiveness or anergy is prevented by contacting T cells with an agent which binds to the cytokine receptor γ chain and stimulates an intracellular signal in the T cell resulting in T cell proliferation. Typically, the agent is an anti-γ chain antibody capable of crosslinking the receptor or a soluble form of natural ligand which binds to the γ chain, such as interleukin-4 or interleukin-7. Alternatively, T cells can be contacted with an agent which acts intracellularly to stimulate phosphorylation of the 116 kD JAK kinase. To induce an immune response against a pathogen, such as a virus, bacteria or parasite in vivo the pathogen or component thereof can be administered in conjunction with an agent which binds to the cytokine receptor γ chain and stimulates an intracellular signal in the T cell. Similarly, tumor immunity can be can be induced in a tumor bearing host in vivo or ex vivo by contacting T cells of the subject in the presence of tumor cells expressing tumor antigens with a γ chain stimulatory agent (e.g., a crosslinking anti-γ chain antibody).

Another embodiment of the invention pertains to methods for inducing unresponsiveness to an antigen in a T cell which expresses a cytokine receptor γ chain. T cells are contacted in vivo or ex vivo in the presence of an antigen with an agent which inhibits delivery of a signal through the cytokine receptor γ chain resulting in T cell unresponsiveness to the antigen. Such agents can act extracellularly to inhibit delivery of a signal through the γ chain, such as an inhibitory or blocking anti-γ chain antibody or an agent which binds a natural ligand of the γ chain to inhibit binding of the ligand to the 7 chain (e.g., an anti-interleukin-2 antibody, an anti-interleukin-4 antibody or an anti-interleukin-7 antibody). Alternatively, the agent can act intracellularly to inhibit delivery of a signal through the cytokine receptor γ chain, such as an agent which inhibits association of the γ chain with the 116 kD JAK kinase or inhibits phosphorylation of the γ chain or the JAK kinase or both. Methods for inducing T cell unresponsiveness are particularly useful for inhibiting transplant rejection and graft-versus-host disease and for treating autoimmune diseases.

Method for identifying agents which stimulate or inhibit delivery of a signal through a cytokine receptor γ chain on a T cell are also within the scope of this invention. These and other embodiments of the invention are described in further detail herein.

DETAILED DESCRIPTION OF THE INVENTION

Figure 1A:
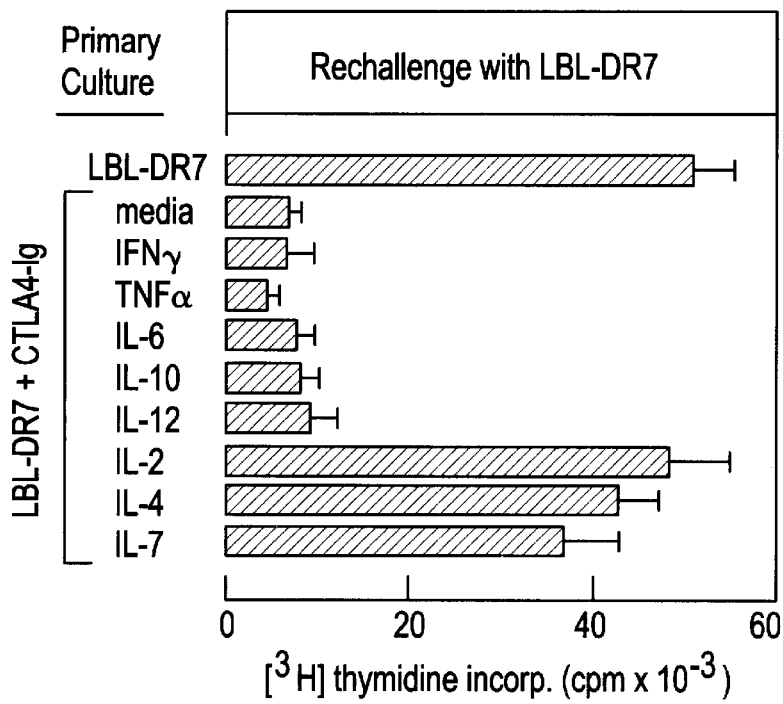
FIGS. 1A–B are graphic representations of the proliferation of DR7-specific T cells upon challenge with LBL-DR7, demonstrating that IL-2, IL-4 and IL-7 can prevent in the induction of T cell anergy. In panel A, the T cells were given an anergic signal by stimulation with antigen (LBL-DR7) while blocking costimulation with CTLA4Ig. In panel B, the T cells were given an anergic signal by stimulation with antigen alone (t-DR7) in the absence of a costimulatory signal.

The term "a common cytokine receptor gamma chain" or "$\gamma_c$" as used herein refers to a polypeptide subunit that is shared by certain cytokine receptors, including the interleukin-2 receptor (IL-2), the interleukin-4 receptor (IL-4) and the interleukin-7 receptor (IL-7). The gamma chain is present in the intermediate affinity (βγ subunits) and high affinity ((αβγ subunit) IL-2 receptors. In one embodiment, $\gamma_c$ is a polypeptide encoded by a nucleotide sequence disclosed in Takeshita, T. et al. (1992) *Science* 257:379–382 and by a gene which maps to human chromosome Xq13. Oligonucleotide primers that can be used to obtain nucleic acid encoding human $\gamma_c$ are described in Noguchi, M. et al. (1993) *Cell* 73:147–157; Puck, J. M. et al. (1993) *Hum. Mol. Genet.* 2:1099–1104; and DiSanto, J. P. et al. (1994) *Eur. J. Immunol.* 24:475–479. In another embodiment, $\gamma_c$ is a polypeptide of about 64 kD.

Various aspects of the invention are described in further detail in the following subsections.

I. Agents that Stimulate through a Common Cytokine Receptor Gamma-chain

A. Cytokines

Cytokines that can stimulate through γc include IL-2, IL-4 and IL-7. Other cytokines which bind to a receptor that utilizes $\gamma_c$ can also be used to stimulate through $\gamma_c$. Cytokines described herein are commercially available. For example, IL-2, IL-4 and IL-7 can be obtained from Genzyme Corp.

B. Anti-γ-chain Antibodies

A stimulatory form of an antibody, or fragment thereof, which binds to $\gamma_c$ can be used to stimulate through $\gamma_c$. A "stimulatory form" of an anti-$\gamma_c$ antibody refers to a form of the antibody which induces an intracellular signal through $\gamma_c$ upon binding to $\gamma_c$. In one embodiment, the stimulatory form of anti-$\gamma_c$ antibody is a soluble antibody that is crosslinked, e.g., by a secondary antibody. In another embodiment, the stimulatory form of anti-$\gamma_c$ is an immobilized form of an antibody, e.g., an antibody bound to a solid support, such as a culture plate or bead.

The stimulatory antibody can be polyclonal antisera or a monoclonal antibody. Antibodies that bind $\gamma_c$ can be prepared by standard techniques known in the art. Animals can be immunized with a $\gamma_c$ "immunogen". The term "immunogen" is used herein to describe a composition containing a $\gamma_c$ peptide or protein as an active ingredient used for the preparation of antibodies against $\gamma_c$. Both soluble and membrane bound CTLA4 protein or peptide fragments are suitable for use as an immunogen. For example, the $\gamma_c$ immunogen can be a cell which expresses a cytokine receptor utilizing $\gamma_c$ (e.g., a cell line expressing a $\gamma_c$-containing form of IL-2R, IL-4R or IL-7R). A preferred cell for use as an immunogen is a T cell, which constitutively expresses $\gamma_c$. Alternatively, the immunogen can be a purified $\gamma_c$ protein or a $\gamma_c$peptide fragment. A $\gamma_c$ protein can be purified from cells by standard techniques or produced recombinantly by expression in a host cell of a nucleic acid encoding $\gamma_c$ (e.g., a nucleic acid having a nucleotide sequence disclosed in Takeshita, T. et al. (1992) *Science* 257:379–382). A $\gamma_c$ peptide fragment can be chemically synthesized based upon the predicted amino acid sequence of a $\gamma_c$ protein (e.g., as disclosed in Takeshita, cited supra). An isolated form of $\gamma_c$protein or peptide can itself be directly used as an immunogen, or alternatively, can be linked to a suitable carrier protein by conventional techniques, including by chemical coupling. The isolated $\gamma_c$ protein can also be covalently or noncovalently modified with non-proteinaceous materials such as lipids or carbohydrates to enhance immunogenecity or solubility. Alternatively, an isolated $\gamma_c$ protein can be coupled with or incorporated into a viral particle, a replicating virus, or other microorganism in order to enhance immunogenicity.

As an alternative to use of a protein or peptide as an immunogen, it is possible to use nucleic acid (e.g., DNA) encoding a $\gamma_c$ protein or peptide as an immunogen for so-called genetic immunization. Thus, the term "immunogen" is also intended to include nucleic acid encoding a protein or peptide against which antibodies are to be raised. To raise antibodies by genetic immunization, an expression vector construct containing nucleic acid encoding the protein of interest (e.g., $\gamma_c$ or a peptide thereof) is delivered intracellularly into the skin of an animal (e.g., mouse) by coating particles (e.g., gold particles) with the construct and injecting the particles into the skin. This results in antigen production in the skin and development of a specific antibody response (see e.g., Tang, D. C. et al. (1992) *Nature* 356:152–154; Eisenbraun, M. D. et al. (1993) *DNA Cell Biol.* 12:791–797; Wang, B. et al. (1993) *DNA Cell Biol.* 12:799–805).

Polycolonal antibodies to $\gamma_c$ can generally be raised in animals by standard methods. Animals can be boosted until the anti-$\gamma_c$ titer plateaus. Also, aggregating agents such as alum can be used to enhance the immune response. The antibody molecules can then be collected from the mammal (e.g., from the blood) and isolated by well known techniques, such as protein A chromatography, to obtain the IgG fraction. To enhance the specificity of the antibody, the antibodies may be purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts. Preferably, the monoclonal antibody used in the subject method is further characterized as immunoreacting with a $\gamma_c$ protein derived from humans.

Monoclonal antibodies useful in the compositions and methods of the invention are directed to an epitope of a $\gamma_c$. A monoclonal antibody to an epitope of $\gamma_c$ can be prepared by using a technique which provides for the production of antibody molecules by continuous cell lines in culture. These include but are not limited to the hybridoma technique originally described by Kohler and Milstein (1975, *Nature* 256:495–497), and the more recent human B cell hybridoma technique (Kozbor et al. (1983) *Immunol Today* 4:72), EBV-hybridoma technique (Cole et al. (1985), *Monoclonal Antibodies and Cancer Therapy,* Alan R. Liss, Inc., pp. 77–96), and trioma techniques. Other methods which can effectively yield monoclonal antibodies useful in the present invention include phage display techniques (Marks et al. (1992) *J Biol Chem* 16007–16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495–97; Brown et al. (1981) *J. Immunol* 127:539–46; Brown et al. (1980) *J Biol Chem* 255:4980–83; Yeh et al. (1976) *PNAS* 76:2927–31; and Yeh et al. (1982) *Int. J. Cancer* 29:269–75). Thus, the monoclonal antibody compositions of the present invention can be produced by the following method, which comprises the steps of:

(a) Immunizing an animal with a $\gamma_c$ immunogen. Preferably, a rodent mammal, such as a rabbit, rat or mouse is used. The mammal is then maintained for a time period sufficient for the mammal to produce cells secreting antibody molecules that immunoreact with the $\gamma_c$ immunogen. Such immunoreaction is detected by screening the antibody molecules so produced for immunoreactivity with a preparation of the immunogen protein. Optionally, it may be desirable to screen the antibody molecules with a preparation of the protein in the form in which it is to be detected by the antibody molecules in an assay, e.g., a membrane-associated form of $\gamma_c$. These screening methods are well known to those of skill in the art, e.g., enzyme-linked immunosorbent assay (ELISA) and/or flow cytometry.

(b) A suspension of antibody-producing cells removed from each immunized mammal secreting the desired antibody is then prepared. After a sufficient time, the mammal is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications,* Hurell (ed.) pp. 51–52 (CRC Press 1982)). Hybridomas produced according to these methods can be propagated in vitro or in vivo (in ascites fluid) using techniques known in the art.

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) Virol. 8:396) supplemented with 4.5 gm/l glucose, 20 mM glutamine, and 20% fetal caf serum. An exemplary inbred mouse strain is the Balb/c.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Such antibodies are the equivalents of the monoclonal and polyclonal antibodies described above, but may be less immunogenic when administered to humans, and therefore more likely to be tolerated by the patient.

Chimeric mouse-human monoclonal antibodies (i.e., chimeric antibodies) reactive with $\gamma_c$ can be produced by recombinant DNA techniques known in the art. For example, a gene encoding the constant region of a murine (or other species) anti-human $\gamma_c$ antibody molecule is substituted with a gene encoding a human constant region. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 Science 240:1041–1043); Liu et al. (1987) PNAS 84:3439–3443; Liu et al. (1987) J. Immunol. 139:3521–3526; Sun et al. (1987) PNAS 84:214–218; Nishimura et al. (1987) Canc. Res. 47:999–1005; Wood et al. (1985) Nature 314:446–449; and Shaw et al. (1988) J. Natl Cancer Inst. 80:1553–1559).

A chimeric antibody can be further "humanized" by replacing portions of the variable region not involved in antigen binding with equivalent portions from human variable regions. General reviews of "humanized" chimeric antibodies are provided by Morrison, S. L. (1985) Science 229:1202–1207 and by Oi et al. (1986) Bio Techniques 4:214. Those methods include isolating, manipulating, and expressing the nucleic acid sequences that encode all or part of an immunoglobulin variable region from at least one of a heavy or light chain. Sources of such nucleic acid are well known to those skilled in the art and, for example, may be obtained from an anti-$\gamma_c$ antibody producing hybridoma. The cDNA encoding the chimeric antibody, or fragment thereof, can then be cloned into an appropriate expression vector. Suitable "humanized" antibodies can be alternatively produced by CDR or CEA substitution (see U.S. Pat. 5,225,539 to Winter; Jones et al. (1986) Nature 321:552–525; Verhoeyan et al. (1988) Science 239:1534; and Beidler et al. (1988) J. Immunol. 141:4053–4060).

As an alternative to humanizing an mAb from a mouse or other species, a human mAb directed against a human protein can be generated. Transgenic mice carrying human antibody repertoires have been created which can be immunized with human a $\gamma_c$ protein or a human cell expressing $\gamma_c$. Splenocytes from these immunized transgenic mice can then be used to create hybridomas that secrete human mAbs specifically reactive with human $\gamma_c$ (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) Nature 368:856–859; Green, L. L. et al. (1994) Nature Genet. 7:13–21; Morrison, S. L. et al. (1994) Proc. Natl. Acad. Sci. USA 81:6851–6855; Bruggeman et al. (1993) Year Immunol 7:33–40; Tuaillon et al. (1993) PNAS 90:3720–3724; Bruggeman et al. (1991) Eur J Immunol 21:1323–1326)

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal anti-$\gamma_c$ antibodies (for descriptions of combinatorial antibody display see e.g., Sastry et al. (1989) PNAS 86:5728; Huse et al. (1989) Science 246:1275; and Orlandi et al. (1989) PNAS 86:3833). After immunizing an animal with a $\gamma_c$ immunogen as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) Biotechniques 11:152–156). A similar strategy can also been used to amplify human heavy and light chain variable regions from human antibodies (Larrick et al. (1991) Methods: Companion to Methods in Enzymology 2:106–110).

In an illustrative embodiment, RNA is isolated from activated B cells from, for example, peripheral blood cells, bone marrow, or spleen preparations, using standard protocols (e.g., U.S. Pat. No. 4,683,202; Orlandi, et al. PNAS (1989) 86:3833–3837; Sastry et al., PNAS (1989) 86:5728–5732; and Huse et al. (1989) Science 246:1275–1281.) First-strand cDNA is synthesized using primers specific for the constant region of the heavy chain(s) and each of the κ and π light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large and diverse antibody display libraries, rapid sorting after each affinity separation round, and easy isolation of the antibody gene from purified display packages. In addition to commercially available kits for generating phage display libraries (e.g., the Pharmacia *Recombinant Phage Antibody System,* catalog no. 27-9400-01; and the Stratagene SurfZAP™ phage display kit, catalog no. 240612), examples of methods and reagents particularly amenable for use in generating a diverse anti-$\gamma_c$ antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science 246:1275–1281;* Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible (Gly$_4$-Ser)$_3$ linker can be used to produce a single chain antibody which can render the display package separable based on antigen affinity. Isolated scFV antibodies immunoreactive with $\gamma_c$ can subsequently be formulated into a pharmaceutical preparation for use in the subject method.

Once displayed on the surface of a display package (e.g., filamentous phage), the antibody library is screened with a $\gamma_c$ protein, or peptide fragment thereof, to identify and isolate packages that express an antibody having specificity for $\gamma_c$. Nucleic acid encoding the selected antibody can be recovered from the display package (e.g., from the phage genome) and subcloned into other expression vectors by standard recombinant DNA techniques.

C. Other Stimulatory Agents

Peptide fragments or modified forms of natural ligands for the common gamma chain of cytokine receptors that stimulate through the gamma chain are also encompassed by the invention. For example, a peptide fragment or modified form of IL-2, IL-4 or IL-7 that retains the ability to stimulate through $\gamma_c$ can be used. Additionally, peptide mimetics and other small molecules (e.g., drugs) that bind to and stimulate through $\gamma_c$. A modified cytokine, peptide fragment, peptide mimetic or small molecule that stimulates through $\gamma_c$ can be identified by screening substances using screening assays as described herein. Alternatively, rational drug design can be used to design a molecule that interact with $\gamma_c$.

Another type of stimulatory agent contemplated by the invention is a nucleic acid encoding a stimulatory ligand for $\gamma_c$. For example, nucleic acid (e.g., DNA) encoding an anti-$\gamma_c$ antibody (or fragment thereof) or cytokine that binds a receptor containing $\gamma_c$ (e.g., IL-2, IL-4, IL-7), can be introduced into cells in vitro, or administered to a subject in vivo, as gene therapy to stimulate T cells responses and prevent the induction of anergy. Recombinant expression vectors for expressing proteins or peptides in cells (e.g., recombinant viral vectors), and nucleic acid delivery mechanisms suitable for gene therapy in vitro or in vivo, are well known in the art. An expression vector encoding a soluble, secreted form of anti-$\gamma_c$ antibody, or a cytokine, can be used to produce within cells a $\gamma_c$-ligand which is then secreted from the cells and binds to a $\gamma_c$-containing surface cytokine receptor on activated T cells (e.g., in culture or in vivo) to prevent induction of anergy.

An alternative type of $\gamma_c$ stimulatory agent for is one which acts intracellularly to trigger a signal mediated by $\gamma_c$. Thus, this agent does not bind to an extracellular portion of $\gamma_c$ or a receptor containing $\gamma_c$, but rather mimics or induces an intracellular signal (e.g., second messenger) associated with ligation of $\gamma_c$. In one embodiment, the agent that acts intracellularly to trigger a signal mediated by $\gamma_c$ stimulates phosphorylation of $\gamma_c$. In another embodiment, the agent stimulates phosphorylation of a 116 kD JAK kinase.

II. Agents that Inhibit Signalling through a Common Cytokine Receptor Gamma-chain A. Anti-γ-chain Antibodies A inhibitory, or blocking, form of an antibody, or fragment thereof, which binds to $\gamma_c$ but does not stimulate through $\gamma_c$ can be used to inhibit signalling through $\gamma_c$. An "inhibitory form" of an anti-$\gamma_c$ antibody refers to a form of the antibody which binds to $\gamma_c$ but does not induces an intracellular signal through $\gamma_c$ upon binding. Moreover, the inhibitory form of anti-$\gamma_c$ antibody preferably inhibits or prevents interaction of $\gamma_c$ with its natural ligands, e.g., inhibits or prevents signalling through $\gamma_c$ by IL-2, IL-4 or IL-7. In one embodiment, the inhibitory form of anti-$\gamma_c$ antibody is a soluble antibody that does not crosslink $\gamma_c$. In another embodiment, the inhibitory form of anti-$\gamma_c$ is an antibody fragment, such as a Fab or Fv fragment, that binds to $\gamma_c$ but does not induce a signal through $\gamma_c$. Inhibitory anti-$\gamma_c$ antibodies, and fragments thereof, can be prepared using standard methodologies, as described above.

B. Anti-cytokine Antibodies

A signal through $\gamma_c$ can also be inhibited using an antibody, or fragment thereof, which neutralizes a cytokine that binds to a receptor containing $\gamma_c$ (e.g., a neutralizing antibody against IL-2, IL-4 or IL-7). The term "neutralizing antibody" refers to an antibody which binds to the cytokine and inhibits or prevents its interaction with its receptor on a T cell. Antibodies against cytokines such as IL-2, IL-4 or IL-7 are commercially available or can be prepared using standard methodologies, as described above.

C. Other Inhibitory Agents

Peptide fragments or modified forms of natural ligands for the common gamma chain of cytokine receptors that inhibit signalling through the gamma chain are also encompassed by the invention. For example, a peptide fragment or modified form of IL-2, IL-4 or IL-7 that retains the ability to bind to $\gamma_c$ but is no longer capable of stimulation through $\gamma_c$ can be used. Additionally, peptide mimetics and other small molecules (e.g., drugs) that bind to $\gamma_c$ and inhibits or prevents binding of natural cytokine ligands to $\gamma_c$ can be used to thereby inhibit intracellular signalling through $\gamma_c$. A modified cytokine, peptide fragment, peptide mimetic or small molecule that inhibits intracellular signalling $\gamma_c$ can be identified by screening substances using screening assays as described herein. Alternatively, rational drug design can be used to design a molecule that blocks binding of natural cytokine ligands (e.g., IL-2, IL-4 or IL-7) with $\gamma_c$.

Another type of inhibitory agent contemplated by the invention is a nucleic acid that is antisense to a nucleic acid encoding $\gamma_c$ (e.g., antisense to a coding or regulatory region of a $\gamma_c$ gene). For example, an antisense nucleic acid (e.g., DNA) can be introduced into cells in vitro, or administered to a subject in vivo, as gene therapy to inhibit T cells responses and induce antigen specific anergy. The antisense nucleic acid can be an oligonucleotide or a recombinant expression vector containing a $\gamma_c$ cDNA or gene, or portion thereof, in an orientation that leads to expression of $\gamma_c$ antisense nucleic acid. Antisense nucleic acid can be introduced into T cells in vitro or in vivo by a delivery mechanism suitable for gene therapy in vitro or in vivo that are known in the art.

An alternative type of $\gamma_c$ inhibitory agent for is one which acts intracellularly to inhibit a signal mediated by $\gamma_c$. Thus, this agent does not block binding of a natural cytokine ligand to the extracellular portion of a $\gamma_c$-containing receptor, but rather inhibits an intracellular signal (e.g., second messenger) associated with ligation of $\gamma_c$. In one embodiment, the agent that acts intracellularly to inhibit a signal mediated by $\gamma_c$ inhibits phosphorylation of $\gamma_c$. In another embodiment, the agent inhibits phosphorylation of a 116 kD JAK kinase. In yet another embodiment, the agent inhibits an interaction, or association, between $\gamma_c$ and the 116 kD JAK kinase.

III. Therapeutic Uses of Gamma Chain Stimulatory Agents

An agent that stimulates an intracellular signal through $\gamma_c$ can be used to stimulate a T cell response to an antigen by preventing induction of antigen specific anergy in the T cell and stimulating proliferation of the T cell. Stimulation through γc may be therapeutically useful for enhancing, prolonging and/or maintaining immune responses in which antigen presentation to a T cell occurs under conditions that naturally may induce T cell anergy. For example, T cells specific for tumor antigens may be susceptible to becoming anergized by stimulation of the T cell with tumor antigens on the surface of tumor cells in the absence of a costimulatory signal (e.g., tumors cells that do not express costimulatory molecules such as B7-1 or B7-2 may anergize T cells, thereby downmodulating anti-tumor responses). Accordingly, antitumor responses may be enhanced by stimulating tumor antigen-specific T cells through $\gamma_c$ in the presence of a tumor antigen-specific signal. For example, a $\gamma_c$ stimulatory agent as described above can be administered to a tumor-bearing subject. Alternatively, T cells from a tumor-bearing subject can be contacted in vitro with tumor cells and a $\gamma_c$ stimulatory agent and then readministered to the subject.

Additionally, T cell responses to pathogens, such as viruses, bacteria, fungi, parasites and the like, may be enhanced and prolonged by administering to a subject harboring the pathogen a $\gamma_c$ stimulatory agent described herein. The efficacy of vaccination may also be increased by stimulating T cells through $\gamma_c$. For example, the vaccine can be administered together with a $\gamma_c$ stimulatory agent to enhance to the immune response against the vaccinating material.

IV. Therapeutic Uses of Gamma Chain Inhibitory Agents

The $\gamma_c$ inhibitory agents of the invention can be used to inhibit a T cell response to an antigen and, moreover, to induce antigen specific T cell anergy such that the T cell will not respond to the antigen upon rechallenge. To inhibit a T cell response and induce anergy, a T cell is contacted with a $\gamma_c$ inhibitory agent in the presence of an antigen specific signal. The responsiveness of a T cell to an antigen can be inhibited according to the methods of the invention either in vitro or in vivo. To inhibit T cells in vitro, T cells are contacted with a $\gamma_c$ inhibitory agent together with a cell presenting antigen to the T cell (e.g., an allogeneic cell to inhibit alloantigen specific responses). To inhibit T cell responses and induce anergy in vivo, a $\gamma_c$ inhibitory agent is administered to a subject. In this case, T cells receive the required antigen stimulation through the TCR/CD3 complex by an endogeneous stimulus in vivo (e.g., an autoantigen or foreign antigen presented by antigen presenting cells in vivo). Alternatively, an antigenic stimulus can be coadministered with the $\gamma_c$ inhibitory agent (e.g., to induce allergen-specific anergy, the allergen can be coadministered with the $\gamma_c$ inhibitory agent). Furthermore, T cell responses can be inhibited non-specifically by delivering a signal through the TCR/CD3 complex with a non-specific reagent, such as an anti-CD3 antibody together with a $\gamma_c$ inhibitory agent.

Additionally or alternatively, in order to inhibit T cell responses and induce anergy in a subject, it may also be beneficial to inhibit or prevent T cells from receiving a costimulatory signal in vivo, such as the costimulatory signal mediated by the interaction of CD28 with either B7-1 or B7-2. Accordingly, in addition to contacting a T cell with a $\gamma_c$ inhibitory agent, the T cell can also be contacted with another agent which inhibits generation of a costimulatory signal in T cells, such as a blocking molecule which binds to CD28, B7-1 or B7-2. Examples of suitable blocking molecules include an anti-CD28 Fab fragment, anti-B7-1 or anti-B7-2 blocking antibodies (i.e., antibodies which block CD28-B7-1/B7-2 interactions but do not induce a costimulatory signal in T cells) and soluble forms of CTLA4, CD28, B7-1 or B7-2 (e.g., a CTLA4Ig fusion protein). Additionally, combinations of blocking molecules, e.g. an anti-B7-1 antibody and an anti-B7-2 antibody may be used.

The methods of the invention for inhibiting a T cell response to an antigen and inducing antigen specific anergy are applicable to a variety of clinical situations where it is desirable to downmodulate T cell responses, as described in greater detail in the subsections below.

A. Organ Transplantation/GVHD: Induction of T cell anergy is useful in situations of cellular, tissue, skin and organ transplantation and in bone marrow transplantation (e.g., to inhibit graft-versus-host disease (GVHD)). For example, anergization of alloreactive T cells may result in reduced tissue destruction in tissue transplantation and long-term graft acceptance without the need for generalized immunosuppression. Typically, in tissue transplants, rejection of the graft is initiated through its recognition as foreign by T cells, followed by an immune reaction that destroys the graft. A $\gamma_c$ inhibitory agent can be administered to a transplant recipient together with the transplanted cells to induce alloantigen specific T cell unresponsiveness. An agent that inhibits a costimulatory signal through CD28/CTLA4Ig, such as CTLA4Ig, can be coadministered with the $\gamma_c$ inhibitory agent.

The approaches described above can similarly be applied to the situation of bone marrow transplantation to specifically anergize alloreactive T cells from donor bone marrow. Donor bone marrow can be incubated prior to transplantation in vitro with cells from the recipient (e.g., hematopoietic cells) and a $\gamma_c$ inhibitory agent. Additional agents that inhibit the generation of a costimulatory signal in the T cells (e.g., anti-B7-1 and/or anti-B7-2 antibodies, CTLA4Ig, etc.) can be included in the incubation. The treated bone marrow is then administered to the recipient, who may further be treated in vivo with a $\gamma_c$ inhibitory agent alone or in combination with an agent that inhibits a costimulatory signal.

The efficacy of a particular $\gamma_c$ inhibitory agent in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., *Science*, 257: 789–792 (1992) and Turka et al., *Proc. Natl. Acad. Sci. USA*, 89: 11102–11105 (1992). In addition, murine models of GVHD (see Paul ed., *Fundamental Immunology*, Raven Press, New York, 1989, pp. 846–847) can be used to determine the effect of inducing T cell unresponsiveness using a $\gamma_c$ inhibitory agent on the development of that disease.

B. Autoimmune Diseases: Induction of antigen specific T cell unresponsiveness by the methods of the invention may also be therapeutically useful for treating autoimmune diseases. Many autoimmune disorders are the result of inappropriate activation of T cells that are reactive against self tissue (i.e., reactive against autoantigens) and which promote the production of cytokines and autoantibodies involved in the pathology of the diseases. Preventing the activation of autoreactive T cells thus may reduce or eliminate disease symptoms. Administration of a $\gamma_c$ inhibitory agent can be used to inhibit T cell responses to autoantigens and, moreover, to induce autoantigen specific anergy. To treat an autoimmune disorder, a $\gamma_c$ inhibitory agent is administered to a subject in need of treatment. Alternatively, for autoimmune disorders with a known autoantigen, the autoantigen can be coadministered to the subject with the inhibitory agent.

This method can be used to treat a variety of autoimmune diseases and disorders having an autoimmune component, including diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of $\gamma_c$ crosslinking agents in preventing or alleviating autoimmune disorders can be determined using a number of well-characterized animal models of human autoimmune diseases. Examples include murine experimental autoimmune encephalitis, systemic lupus erythematosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

C. Allergy: The IgE antibody response in atopic allergy is highly T cell dependent and, thus, inhibition of allergen specific T cell responses and induction of allergan specific anergy may be useful therapeutically in the treatment of allergy and allergic reactions. For example, a $\gamma_c$ inhibitory agent can be administered to an allergic subject exposed to an allergen to induce apoptosis in allergen specific T cells, thereby downmodulating allergic responses in the subject. Administration of a $\gamma_c$ inhibitory agent to an allergic subject may be accompanied by enviromental exposure to the allergen or by coadministration of the allergen to the subject. Allergic reactions may be systemic or local in nature, depending on the route of entry of the allergen and the pattern of deposition of IgE on mast cells or basophils. Thus, it may be necessary to inhibit T cell responses locally or systemically by proper administration of a $\gamma_c$ inhibitory agent. For example, in one embodiment, a $\gamma_c$ inhibitory agent and an allergen are coadminstered subcutaneously to an allergic subject.

D. Induction of Antigen-Specific Anergy: The methods of the invention for inducing T cell unresponsiveness can essentially be applied to any antigen (e.g., protein) to anergize T cells to that antigen in a subject. Thus, an antigen of interest to which T cells are to be anergized can be administered to a subject together with a $\gamma_c$ inhibitory agent. The antigen may be administered in a soluble form or attached to a carrier or support (e.g., a bead). This basic approach has widespread application as an adjunct to therapies which utilize a potentially immunogenic molecule for therapeutic purposes. For example, an increasing number of therapeutic approaches utilize a proteinaceous molecule, such as an antibody, fusion protein or the like, for treatment of a clinical disorder. A limitation to the use of such molecules therapeutically is that they can elicit an immune response directed against the therapeutic molecule in the subject being treated (e.g., the efficacy of murine monoclonal antibodies in human subjects is hindered by the induction of an immune response against the antobodies in the human subject). The method of the invention for inducing antigen specific T cell unresponsiveness can be applied to these therapeutic situations to enable long term usage of the therapeutic molecule in the subject without elicitation of an immune response. For example, to anergize T cells responsive to a therapeutic antibody (e.g., a murine mAb which typically activates T cells specific for the antibody in a human subject), the therapeutic antibody is administered to a subject (e.g., human) together with a $\gamma_c$ inhibitory agent. The method may additionally involve administration of an agent that inhibits a CD28/CTLA4-mediated costimulatory signal, such as CTLA4Ig.

V. Administration of Therapeutic Forms of Gamma Chain Stimulatory or Inhibitory Agents The agents of the invention are administered to subjects in a biologically compatible form suitable for pharmaceutical administration in vivo to stimulate or inhibit T cell responses. By "biologically compatible form suitable for administration in vivo" is meant a form of the agent to be administered in which any toxic effects are outweighed by the therapeutic effects of the agent. The term subject is intended to include living organisms in which an immune response can be elicited, e.g., mammals. Examples of subjects include humans, monkeys, dogs, cats, mice, rats, and transgenic species thereof. Administration of an agent of the invention as described herein can be in any pharmacological form including a therapeutically active amount of γc stimulatory or inhibitory agent alone or in combination with another therapeutic molecule (e.g., an agent which stimulates or inhibits a signal through a receptor (e.g., CD28/CTLA4) for a costimulatory molecule (e.g., B7-1 and/or B7-2), such as stimulatory or blocking antibodies to CD28, B7-1 or B7-2 blocking antibodies, CTLA4Ig etc.) and a pharmaceutically acceptable carrier. Administration of a therapeutically active amount of the therapeutic compositions of the present invention is defined as an amount effective, at dosages and for periods of time necessary to achieve the desired result. For example, a therapeutically active amount of an $\gamma_c$ stimulatory or inhibitory agent may vary according to factors such as the disease state, age, sex, and weight of the individual, and the ability of agent to elicit a desired response in the individual. Dosage regimens may be adjusted to provide the optimum therapeutic response. For example, several divided doses may be administered daily or the dose may be proportionally reduced as indicated by the exigencies of the therapeutic situation.

The active compound may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer an agent by other than parenteral administration, it may be necessary to coat the ligand with, or co-administer the ligand with, a material to prevent its inactivation. An agent may be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polytheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

When the active compound is suitably protected, as described above, the compound may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

VI. Screening Assays

Another aspect of the invention pertains to screening assays for identification of agents that inhibit or stimulate signalling through $\gamma_c$. In one embodiment, a method for identifying an agent that inhibits signalling through $\gamma_c$ involves: contacting a T cell that expresses a cytokine receptor containing $\gamma_c$ (e.g., IL-2R, IL-4R, IL-7R) with an first agent that stimulates a primary activation signal (e.g., an anti-CD3 antibody or an antigen presented by an antigen presenting cell) and a second agent that stimulates a signal through $\gamma_c$ (e.g., a cytokine such as IL-2, IL-4 or IL-7 or an antibody that crosslinks $\gamma_c$) in the presence and absence of a substance to be tested. The proliferation of the T cell is measured and an substance that inhibits signalling through $\gamma_c$ is identified based upon the ability of the substance to inhibit proliferation of the T cell (i.e., the proliferative response of the T cell is inhibited in the presence of the substance compared to the proliferative response in the absence of the substance). T cell proliferation can be measured by standard assays, such as tritiated thymidine incorporation. Alternatively, following stimulation of the T cell with the first and second agents described above in the presence and absence of a substance to be tested, an intracellular response can be measured, such as the association between $\gamma_c$ and the 116 kD JAK kinase, phosphorylation of $\gamma_c$ or phosphorylation of the 116 JAK kinase. A substance that inhibits signalling through $\gamma_c$ can be identified based upon the ability of the substance to inhibit an association between $\gamma_c$ and the 116 kD JAK kinase, phosphorylation of $\gamma_c$ or phosphorylation of the 116 JAK kinase. The association between $\gamma_c$ and the 116 kD JAK kinase can be measured by coimmunoprecipitation assays, as described in Example 3. The phosphorylation of $\gamma_c$ and the 116 JAK kinase can be assayed using anti-phosphotyrosine antibodies, as described in Example 3.

Alternatively, screening assays can be used to identify agents that stimulate an intracellular signal through gc. In one embodiment, such a screening assays involves contacting a T cell that expresses contacting a T cell that expresses a cytokine receptor containg $\gamma_c$ (e.g., IL-2R, IL-4R, IL-7R) with an agent that stimulates a primary activation signal (e.g., an anti-CD3 antibody or an antigen presented by an antigen presenting cell) without inducing a costimulatory signal through CD28/CTLA4, in the presence and absence of a substance to be tested, followed by measurement of T cell proliferation. Stimulation of the T cell only the agent that stimulates a primary activation signal will result in induction of anergy in the T cell and a lack of T cell proliferation. A substance which stimulates a signal through $\gamma_c$ can be identified based upon its ability to prevent induction of anergy in the T cell. That is, in the presence of the stimulatory substance, the T cell will proliferate and will respond to antigen upon rechallenge. Alternatively, an intracellular response, such as phosphorylation of $\gamma_c$ or the 116 kD JAK kinase can be measured. An agent that stimulates through γc can be identified based upon the ability of the substance to induce phosphorylation of $\gamma_c$ or the 116 kD JAK kinase.

In another embodiment, a two-hybrid assay system such as that described in U.S. Pat. No. 5,283,173 and PCT application WO 94/10300 is used to identify agents that inhibit an interaction between $\gamma_c$ and a 116 kD JAK kinase. Kits for performing the two-hybrid assay system are commercially available from Clontech, Palo Alto, Calif. Alternatively, glutathione-S-transferase fusion proteins of γc and/or the 116 kD JAK kinase can be prepared and used to identify agents that inhibit an interaction between γc and a 116 kD JAK kinase. For example, a GST fusion of one protein is made, incubated with a labeled preparation of the other protein, in the presence and absence of a substance to be tested, and the γc-116 kD JAK kinase complex precipitated with glutathione-agarose. A substance which inhibits an interaction between γc and the 116 kD JAK kinase can be identified based upon the ability of the substance to reduce the amount of labeled protein that is precipitated with the GST fusion protein.

This invention is further illustrated by the following examples which should not be construed as limiting. The contents of all references, patents and published patent applications cited throughout this application are hereby incorporated by reference.

EXAMPLE 1

IL-2, IL-4 and IL-7 Prevent the Induction of Anergy in T Cells

In the Examples, a human alloantigen specific T cell clonal model system was used. HLA-DR7 alloantigen-specific T-cell clones TC-3 and TC-4 (CD4$^+$,CD8$^-$, CD28$^+$, B7$^-$) were generated using standard methodology. In various experiments, the DR7-specific T cell clones were cultured with a DR7$^+$ lymphoblastoid cell line (LBL-DR7) or NIH-3T3 cells transfected to express DR-7 alone (t-DR7) or DR-7 and B7-1 (t-DR7/B7-1). LBL-DR7 is an EBV transformed lymphoblastoid B-cell line, which is homozygous for HLA-DR7 and strongly expresses B7-1, B7-2, LFA-1, LFA-3 and ICAM-1. NIH-3T3 cell transfectants are described in Gimmi, C. D. et al. (1993) *Proc. Natl. Acad. Sci. USA* 90:6586. In various experiments, different cytokines or antibodies were added to the culture. Before each experiment, T-cell clones were rested for 10 to 14 days in L-2 without alloantigen restimulation. Prior to use, cells were cultured overnight without stimulus or IL-2.

In a first series of experiments, alloantigen-specific (i.e., DR7-specific) T cell clones were incubated in primary culture with 1) LBL-DR7, 2) LBL-DR7 plus CTLA4-Ig, either in media or in the presence of various cytokines, 3) t-DR7/B7-1 or 4) t-DR7 either in media or in the presence of various cytokines. The cytokines used in the experiments, and the concentration of cytokine used, are as follows: IL-2 (50 U/ml); IL-4 (5 ng/ml) (Genzyme, Cambridge, Mass.); IL-6 (30 ng/ml) (Genzyme); IL-7 (10 ng/ml) (Genzyme); IL-12 (10 U/ml) (Genetics Institute, Cambridge, Mass.); TNFα (500 U/ml) (Genzyme); IFNγ (500 U/ml) (Biogen, Cambridge, Mass.). Prior to use, LBL-DR7 cells and NIH 3T3 transfectants were treated with mitomycin-C. In some experiments, LBL-DR7 cells were irradiated (9600 rads). T cell clones were cultured in a primary culture for 24 hrs. Following primary culture, T cells were separated from LBL-DR7 by Ficoll and from NIH 3T3 transfectants by Percoll, and recultured in media without IL-2 for 12 hrs. Each population was subsequently rechallenged with LBL-DR7 stimulators in secondary culture. Samples were cultured and proliferation was measured by [$^3$H]-thymidine (1 μCi) incorporation.

Figure 1B:
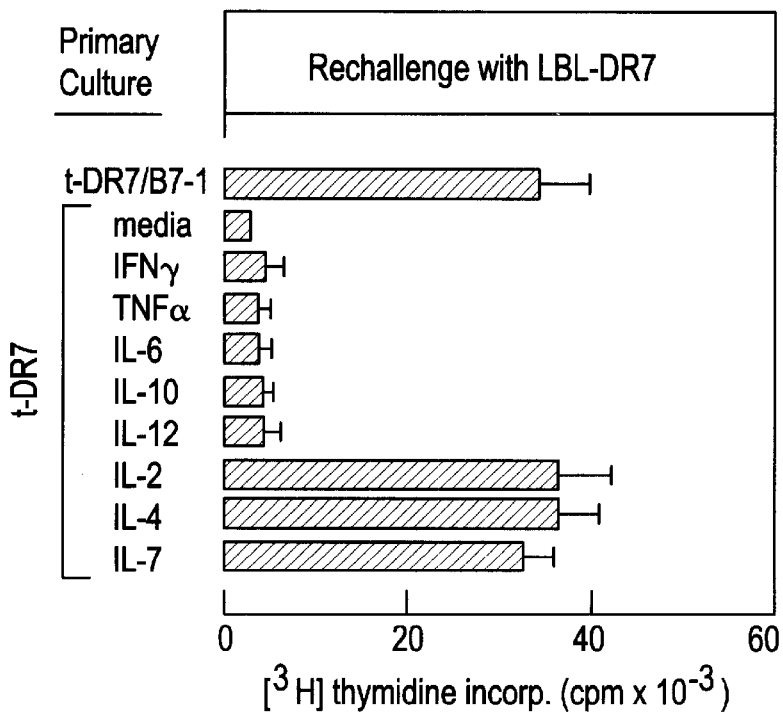

The results for T cells stimulated with LBL-DR7 are shown in FIG. 1, panel A. The results for T cells stimulated with NIH-3T3 transfectants are shown in FIG. 1, panel B. Results represent response in rechallenge and are expressed as the means of triplicate cultures.

Identical results were obtained with both TC-3 and TC-4 clones. Following primary culture with either a HLA-DR7 homozygous lymphoblastoid cell line (LBL-DR7) or transfectants expressing HLA-DR7 and the B7-1 costimulatory molecule (t-DR7/B7-1), HLA-DR7-specific alloreactive T cell clones significantly proliferated to secondary rechallenge with LBL-DR7 cells. In contrast, when primary culture of the T cell clones was with either LBL-DR7 cells in the presence of CTLA4-Ig, to block B7 family mediated costimulation, or with transfectants expressing HLA-DR7 alone (t-DR7), they were anergized and did not respond on rechallenge with LBL-DR7 cells. Addition of varying concentrations of IFN-γ, TNF-α, IL-6, L-10, or IL-12 to the primary culture with either LBL-DR7 plus CTLA4-Ig or t-DR7 did not prevent the induction of anergy. This was somewhat surprising since INF-γ, IL-6, IL-10, and IL-12 each alone could induce proliferation of the T cell clone. In contrast, addition of IL-2, IL-4 or IL-7 to the primary culture with either LBL-DR7 plus CTLA4-Ig or t-DR7, prevented the induction of energy.

EXAMPLE 2

Stimulation of the Common γ-Chain of the IL-2, IL-4 and IL-7 Receptors Prevents the Induction of Anergy In T Cells Since only the addition of exogenous IL-2, IL-4, and IL-7 prevented the induction of alloantigen-specific anergy (see Example 1) and since these cytokines share the $\gamma_c$, it was examined whether $\gamma_c$ signaling during primary culture might be associated with the prevention of anergy. To address this issue, specific mAbs were employed. The various antibodies were directed against: 1) the α or β chains of IL-2 receptor (αIL-2Rα, and αIL-2Rβ), 2) the chains of the conventional receptor of IL-4 or IL-7 (αIL-4R and αIL-7R), and 3) the common γ chain shared by IL-2, IL-4, and IL-7 receptors (αγ$_c$). Primary culture of T cell clones was with either LBL-DR7 plus CTLA4-Ig or t-DR7, together with each of the above mAbs crosslinked with rabbit anti-mouse Ig (RaM). Primary culture and rechallenge were performed as described in Example 1. Antibodies against IL-2Rα (IgG2a) (D. A. Fox, et al. (1984) *J. Immunol.* 133:1250) (Coulter), IL-2Rβ (IgG) (M. Kamio, et al. (1990) *Int. Immunol.* 2:521) (Coulter), IL-4R (IgG1) (W. C. Fanslow, et al. (1993) *Blood* 81:2998) (Genzyme), IL-7R (IgG1) (R. G. Goodwin, et al. (1990) *Cell* 60:941) (Genzyme) or γ$_c$ (IgG1) (T. Nakarai, et al. (1994) *J Exp Med* 180:241) and RaM were all used at a concentration of 10 μg/ml. Identical results were obtained when biotinylated γ$_c$ antibody was used and crosslinking was performed with streptavidin (10 μg/ml), in biotin free RPMI. Identical results were obtained with both TC-3 and TC-4 clones.

Figure 2A:
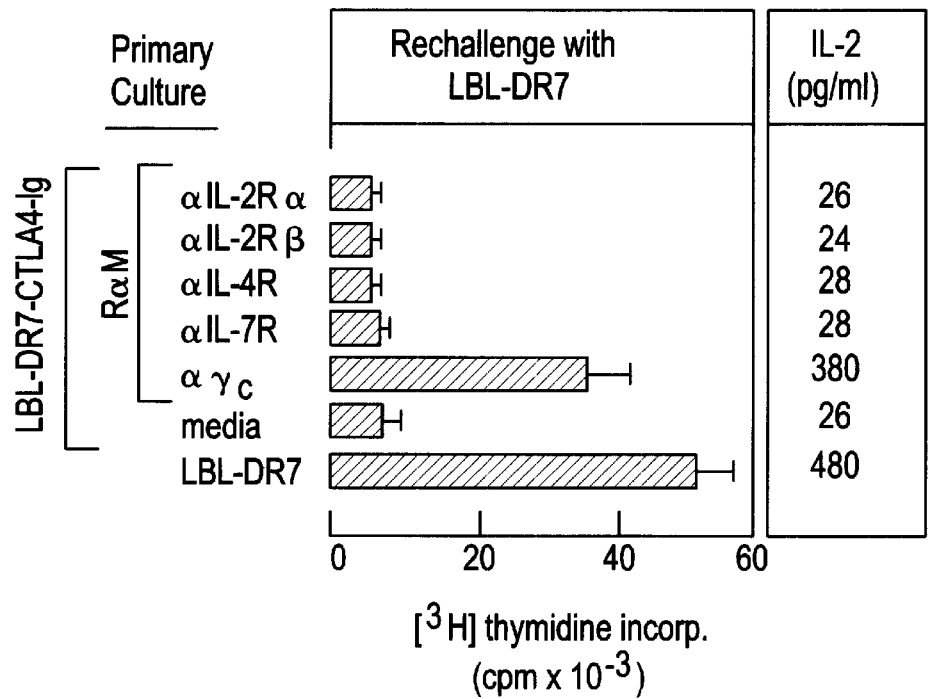
FIGS. 2A–B are graphic representations of the proliferation of DR7-specific T cells upon challenge with LBL-DR7, demonstrating that crosslinking of the common γ-chain of the IL-2, IL-4 and IL-7 receptors prevents in the induction of T cell anergy. In panel A, the T cells were given an anergic signal by stimulation with antigen (LBL-DR7) while blocking costimulation with CTLA4Ig. In panel B, the T cells were given an anergic signal by stimulation with antigen alone (t-DR7) in the absence of a costimulatory signal.
Figure 2B:
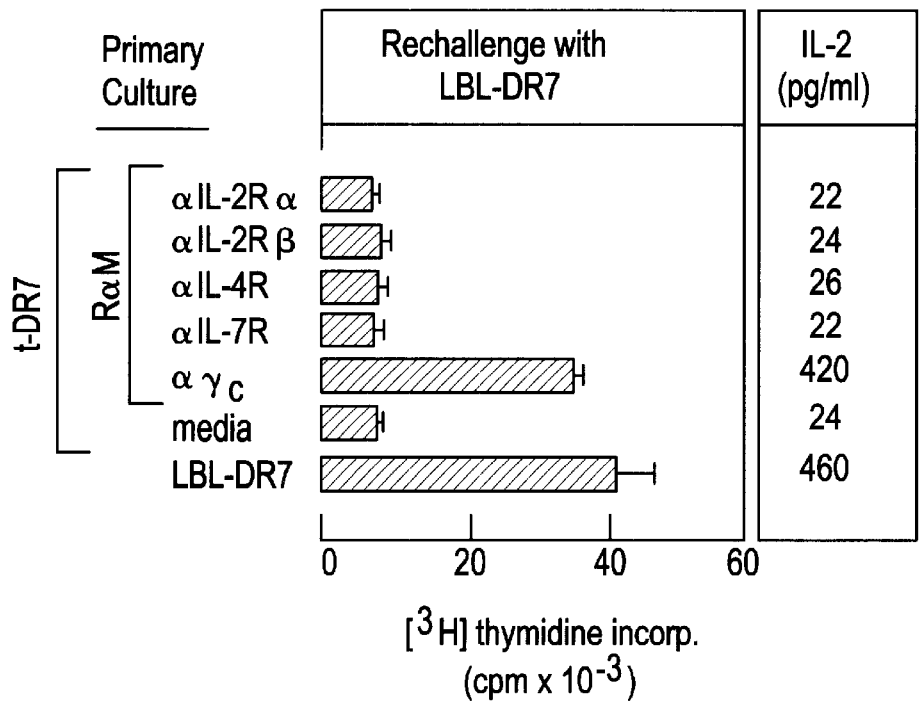
Figure 3A:
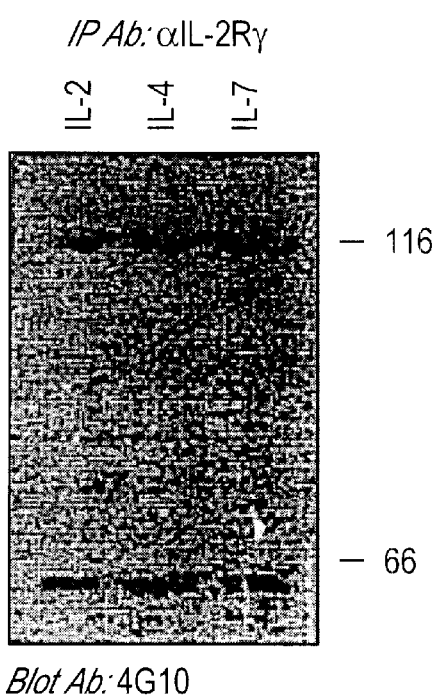
FIGS. 3A–E are photographs of immunoprecipitation filters, depicting the association and phosphorylation of $\gamma_c$ and a 116 kD JAK kinase upon stimulation of T cells with IL-2, IL4 or IL-7. Panel A depicts coimmunoprecipitation of the 116 kD JAK kinase with $\gamma_c$ by an anti-IL-2Rγ antibody and phosphorylation of both $\gamma_c$ and the 116 kD JAK kinase by binding of an anti-phosphotyrosine antibody (4G10). The 116 kD protein is a JAK kinase family member, demonstrated by binding of an anti-JAK antibody (R80) (Panel B) but does not bind antibodies against JAK 1 (Panel C) JAK 2 (Panel D) or Tyk2 (Panel E).
Figure 3B:
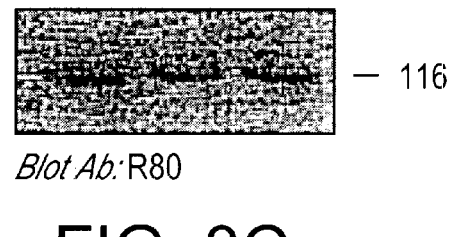
Figure 3C:
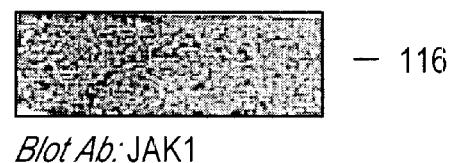
Figure 3D:
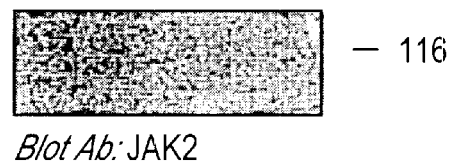
Figure 3E:
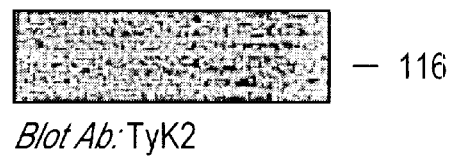

The results for T cells stimulated with LBL-DR7 are shown in FIG. 2, panel A. The results for T cells stimulated with t-DR7 are shown in FIG. 2, panel B. Crosslinking of either IL-2Rα, IL-2Rβ, IL-4R or IL-7R during the primary culture did not prevent the induction of anergy. In contrast, crosslinking of γ$_c$ during the primary culture prevented the induction of anergy and resulted in both proliferation and IL-2 secretion on rechallenge, comparable to that observed with non-anergized control cells. These results demonstrate that in the presence TCR signaling, common γ chain crosslinking is sufficient to prevent the induction of anergy. Moreover, these data support the hypothesis that the common effect of IL-2, IL-4 and IL-7 to prevent the induction of anergy is mediated through a γ$_c$ signaling pathway.

EXAMPLE 3

Prevention of Anergy Induction in T Cells is Associated with Phosphorylation of the 116 kD JAK Kinase To examine whether a common signaling pathway mediated via the γ$_c$ could be identified following IL-2, IL-4 and IL-7 stimulaton, T cell clones were cultured with either IL-2, IL-4, or IL-7 and cell lysates immunoprecipitated with anti-γ$_c$ mAb. Alloantigen-specific human helper T cell clone were incubated in D-MEM serum-free media without IL-2 for 12 hours and subsequently stimulated for 15 min with media, IL-2, IL-4, IL-7, TNFα, or IL-12. Cells were lysed with lysis buffer containing 10 mM Tris-HCl, pH 7.6, 5 mM EDTA, 50 mM NaCl, 30 mM sodium pyrophosphate, 50 mM NaFl, 1 mM sodium orthovanadate, 5 μg/ml aprotinin, 1 μg/ml pepstatin, and 2 μg/ml soybean trypsin inhibitor, 1 mM phenylmethylsulfonyl fluoride and 0.5% NP-40 (Sigma). For the experiment shown in FIG. 3, panel A, immunoprecipitations were conducted with anti-γ$_c$ antibody, immune complexes were isolated on protein A-sepharose, washed three times with lysis buffer and analysed on 6–12% gradient SDS-PAGE. Proteins transfered to nitrocellulose membrane were blocked for 1 hr in room temperature by shaking in TBST (20 mM Tris HCl, pH 7.6, 137 mM NaCl, 0.1% Tween-20) containing 10% bovine serum albumine. For detection of phosphotyrosine proteins, the blots were incubated with 4G10 anti-phosphotyrosine monoclonal antibody (1:2000) for 60 min at room temperature. The blots were washed three times with wash buffer (50 mM Tris-HCl, pH 7.6, 200 mM NaCl, 0.1% Tween-20), followed by 60 min incubation with horseradise peroxidase conjugated-sheep anti-mouse IgG (1:5000) (Amersham, Arlington Heights, Ill.). The blots were washed three times with wash buffer followed by incubation with the enhanced chemiluminescence substrate (Amersham), exposed to X-ray film and developed. Following ECL immunodepletion, the immunoblot was stripped by incubation in 62.5 mM Tris-HCl (pH 6.8), 3% w/v SDS and 100 mM β-mercaptoethanol at 50° C. for 1 hr. For the other experiments shown in FIG. 3, membranes were blocked and reprobed with either anti-JAK (R80)(1:1000) antibody (panel B), or peptide specific mAbs for JAK1 (panel C), JAK2 (panel D) and Tyk2 (panel E), washed and detected as described above.

FIG. 3, panel A, shows that the 64 kD band of γ$_c$ is co-precipitated with a band of 116 kD. Western blotting with anti-phosphotyrosine mAb demonstrated phosphorylation of both the 64 kD and 116 kD bands on a tyrosine residue(s). These results suggest that γ$_c$ is physically associated with a 116 kD molecule, which is co-phosphorylated with γ$_c$ upon stimulation of T cells with IL-2, IL-4 or IL-7. Moreover, these results support the critical role of γ$_c$ in IL-2R, IL-4R and IL-7R signal transduction.

To determine whether the 116 kD phosphorylated substrate was a member of the Janus family of protein kinase (JAK kinases), a polyclonal antibody (R80) directed against the functional, carboxy-terminal kinase domain (JH1) of the JAK family members was used. Blotting with the antibody to the common JAK kinase (R80), following immunoprecipitation with the anti-γ$_c$ mAb demonstrated that the 116 kD band which was co-precipitated with the γ$_c$, was recognized by R80 (FIG. 3, panel B). In contrast, re-blotting of the immunoblot with peptide-specific mAbs for JAK1, JAk2 and Tyk2, demonstrated that the 116 kD band was not recognized by any of those mAbs (FIG. 3, panels, C, D and E, respectively). These results indicate that γ$_c$ signaling results in phosphorylation of a 116 kD JAK kinase family member, distinct from JAK1, JAK2 and Tyk2.

Figure 4B:
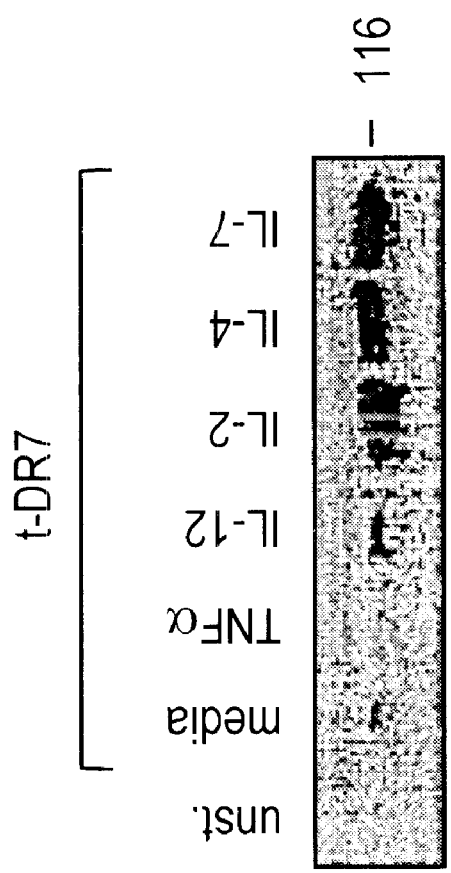
FIG. 4B is a photograph of an immunoprecipitation filter, depicting phosphorylation of the 116 kD JAK kinase upon stimulation of DR7-specific T cells with an antigenic signal (tDR7) and either IL-2, IL-4 or IL-7.
Figure 4A:
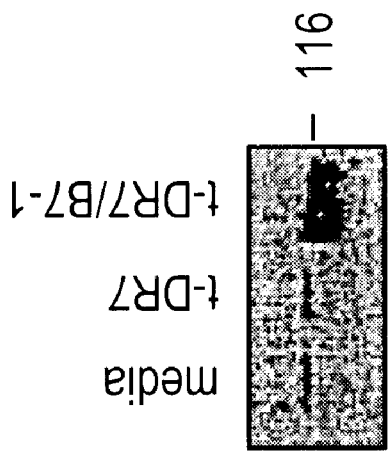
FIG. 4A is a photograph of an immunoprecipitation filter, depicting phosphorylation of the 116 kD JAK kinase upon stimulation of DR7-specific T cells with an antigenic signal and a costimulatory signal (t-DR7/B7-1) but not an antigenic signal alone (t-DR7).

Since γ chain signaling resulted in phosphorylation of the 116 kD JAK kinase and prevention of anergy, it was examined whether phosphorylation of the 116 kD JAK kinase was induced under various conditions that prevented the induction of anergy. T cell clones were cultured with either media, t-DR7 or t-DR7/B7-1 for 24 hrs. Following culture, T cells were separated from transfectants by Percoll gradient, lysed, and then immunoprecipitated with R80. Cell lysates were prepared, immunoprecipitated with the common JAK (R80) antibody and immunoblot analysis with 4G10 anti-phosphotyrosine monoclonal antibody (1:2000) was performed as described above. t-DR7/B7-1 culture (non-anergizing conditions) resulted in significant phosphorylation of 116 kD protein (FIG. 4, panel A). In contrast, following t-DR7 culture (anergizing conditions), there was no significant increase in phosphorylation of 116 kD protein compared to media control. Culture of T cell clones with t-DR7 cells in the presence of IL-2, IL-4, or IL-7, but not TNFα or IL-12, not only prevented the induction of anergy, but also resulted in phosphorylation of 116 kD protein (FIG. 4, panel B).

The above results demonstrate that γ$_c$ signaling represents a critical step in the prevention of anergy. Regardless of the distal signaling mechanism(s), the functional outcome of γ$_c$ crosslinking appears to be critical for the prevention of anergy since crosslinking of other receptor chains does not induce this functional effect. These results underscores the central role of γ$_c$ in the regulation of T cell survival and function. Since virtually all murine and human thymocytes express $\gamma_c$ (Cao, X. et al. (1993) *Proc. Natl. Acad. Sci.* 90:8464), it is not surprising that the redundancy of cytokines that can signal via $\gamma_c$, protect the host against the induction of T cell anergy and/or clonal deletion. Since CD28 costimulation both induces IL-2 accumulation and augments IL-2 receptor expression, this pathway is highly efficient in prevention the induction of anergy ia IL-2, whereas other cytokines capable of signaling via $\gamma_c$ might be equally efficient at preventing the induction of anergy in other microenvironments. For example, the production of IL-7 by marrow stromal cells (Henney, C. S. (1989) *Immunol Today* 10:170) provides a mechanism to prevent the induction of anergy in the marrow microenvironment. In addition, more recently described cytokines including IL-13 and IL-15 may also signal via $\gamma_c$, and therefore, extend the repetoire of cytokines which can prevent the induction of anergy.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for stimulating T cell responsiveness, comprising contacting a T cell which expresses a cytokine receptor γ chain with an anti-γ chain antibody which binds to and transduces a signal via the γ chain such that T cell responsiveness is stimulated.

2. The method of claim 1, wherein the T cell has received a primary activation signal in the absence of a costimulatory signal.

3. The method of claim 1, wherein the T cell is contacted in vivo with the anti-γ chain antibody.

4. The method of claim 1, further comprising contacting the T cell with an agent which stimulates a primary activation signal in the T cell.

5. The method of claim 4, further comprising contacting the T cell with an agent which stimulates a costimulatory signal in the T cell.

6. The method of claim 4, wherein the agent which stimulates a primary activation signal in the T cell is an antigen.

7. The method of claim 6, wherein the antigen is a pathogen or portion thereof selected from the group consisting of a virus, a bacteria, and a parasite.

8. The method of claim 6, wherein the antigen is a tumor antigen.

9. The method of claim 6, wherein the T cell is contacted with the antigen in vivo.

10. The method of claim 2, wherein the T cell is contacted with the agent in vitro.

11. A method for stimulating responsiveness in an anergic T cell, comprising contacting said T cell with an anti-γ chain antibody which transduces a signal via the cytokine receptor γ chain such that T cell responsiveness is stimulated.

* * * * *